United States Patent [19]

Kees, Jr.

[11] Patent Number: 4,660,558

[45] Date of Patent: Apr. 28, 1987

[54] ANEURYSM CLIP AND METHOD OF MANUFACTURE

[76] Inventor: George Kees, Jr., 104 North St., Wilder, Ky. 41071

[21] Appl. No.: 815,231

[22] Filed: Dec. 31, 1985

[51] Int. Cl.$^4$ .............................................. A61B 17/12
[52] U.S. Cl. .................................... 128/325; 128/346; 24/546
[58] Field of Search ............... 128/326, 325, 346, 354; 24/547, 551, 546, 561, 562, 566; 294/99.1

[56] References Cited

U.S. PATENT DOCUMENTS

| | | | |
|---|---|---|---|
| 1,741,457 | 12/1929 | Glass | 128/325 |
| 2,704,071 | 3/1955 | Becker | 128/346 X |
| 3,827,438 | 8/1974 | Kees | 128/325 X |
| 4,024,868 | 5/1977 | Williams | 128/325 |
| 4,360,023 | 11/1982 | Sugita et al. | 128/325 |
| 4,444,187 | 4/1984 | Perlin | 128/325 X |
| 4,484,581 | 11/1984 | Martin et al. | 128/325 X |
| 4,556,060 | 12/1985 | Perlin | 128/346 X |

Primary Examiner—Michael H. Thaler
Attorney, Agent, or Firm—James W. Pearce; Roy F. Schaeperklaus

[57] ABSTRACT

An aneurysm clip which includes an elongated main section providing a central spring portion, jaw forming end portions, and connecting portions between the central spring portion and the jaw forming portions. Jaw addition sections are mounted on opposite sides of the jaw end portions. The connecting portions cross each other and each jaw end portion is opposed to and urged toward one of the jaw addition sections. A guide end portion of one of the jaw addition sections extends from an associated jaw and is engageable by a connecting portion associated with the other jaw to hold the jaws in alignment.

3 Claims, 11 Drawing Figures 4,660,558

ANEURYSM CLIP AND METHOD OF MANUFACTURE

BACKGROUND OF THE INVENTION

This invention relates to aneurysm clips. More particularly, this invention relates to an aneurysm clip having a guide keeping the jaws in cooperative alignment, which clip may be made in such small sizes as are suitable for use in connection with aneurysms on small blood vessels which clips previously available were unsuited for closing due to size of the vessel or because of the confined nature of the location of the aneurysm. The clip has double width jaws and is fabricated from two pieces of spring wire.

An object of this invention is to provide an aneurysm clip of small size which represents an improvement in the type of clip shown and claimed in applicant's U.S. Pat. No. 3,827,438.

SUMMARY OF THE INVENTION

Briefly, this invention provides an aneurysm clip formed from two lengths of spring wire, a main section formed from a single length of spring wire and a jaw addition and guide end section formed from a second length of spring wire. A central portion of the main section of the clip forms a spring. The jaw addition section (of the jaw addition and guide section) and one end portion of the main section form one cooperating clamping jaw and the return bent portion and the adjacent other end portion of the main section form a second cooperating clamping jaw, which jaws are connected to the spring portion by connecting portions. A guide end portion of the jaw addition section extends generally toward the central spring portion from an associated jaw and is engageable by a connecting portion associated with the other jaw to hold the jaws in alignment. The jaws may be shortened to desired length by cutting portions off of the free ends and eliminating any sharp edges left by the cut-off operation.

The above and other objects and features of the invention will be apparent to those skilled in the art to which this invention pertains from the following detailed description and the drawings, in which:

DESCRIPTION OF PRESENTLY PREFERRED EMBODIMENT

Figure 1:
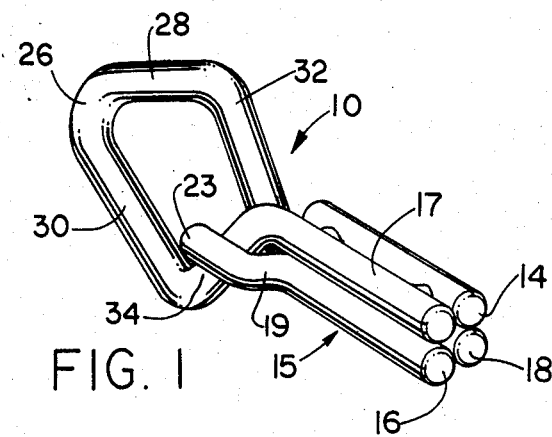
FIG. 1 is a perspective view of an aneurysm clip constructed in accordance with an embodiment of this invention.
Figure 2:
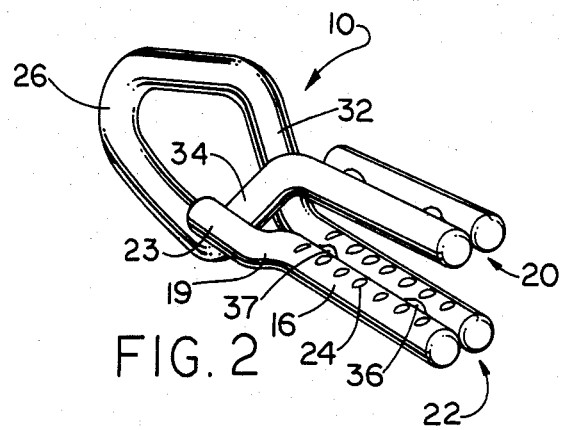
FIG. 2 is a perspective view of the aneurysm clip in open position.
Figure 3:
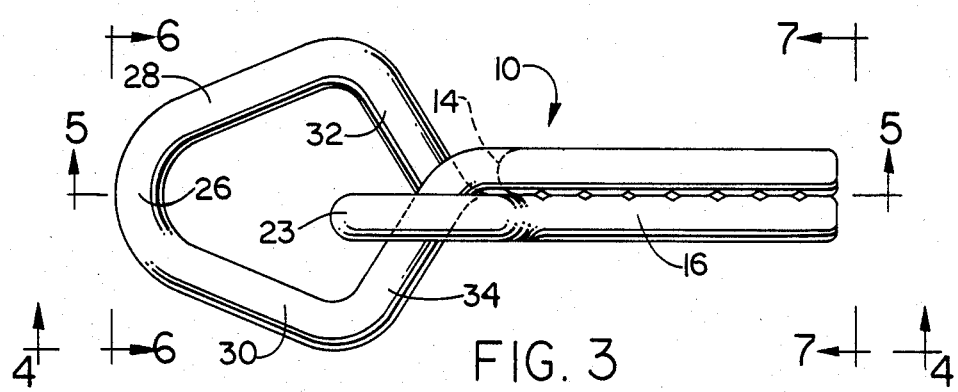
FIG. 3 is a plan view of the aneurysm clip.
Figure 4:
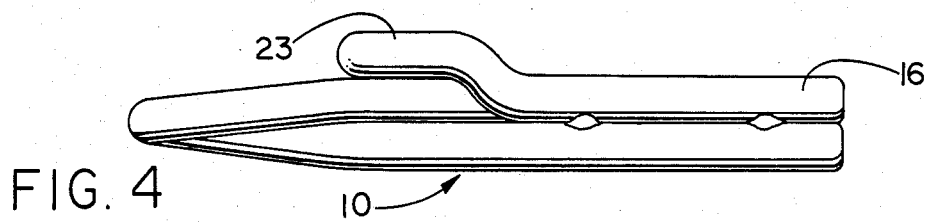
FIG. 4 is a view in side elevation of the aneurysm clip, looking in the direction of the arrows 4—4 in FIG. 3.
Figure 5:
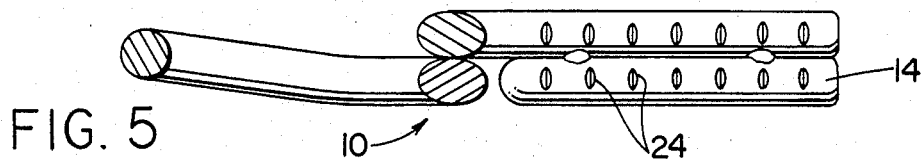
FIG. 5 is a view in section taken on the line 5—5 in FIG. 3.
Figure 6:
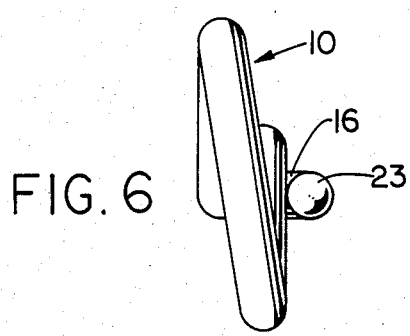
FIG. 6 is a view in end elevation of the clip looking in the direction of the arrows 6—6 in FIG. 3.

In the following detailed description and the drawing, like reference characters indicate like parts.

In FIGS. 1-7 inclusive is shown an aneurysm clip 10 constructed in accordance with an embodiment of this invention. The clip 10 includes a main section 12, which is formed from an elongated length of spring metal (FIGS. 8, 9, 10 and 11) of circular cross section, and a short length or guide and jaw addition section 15, which is also an elongated length of spring metal (FIG. 8) of circular cross section.

Figure 10:
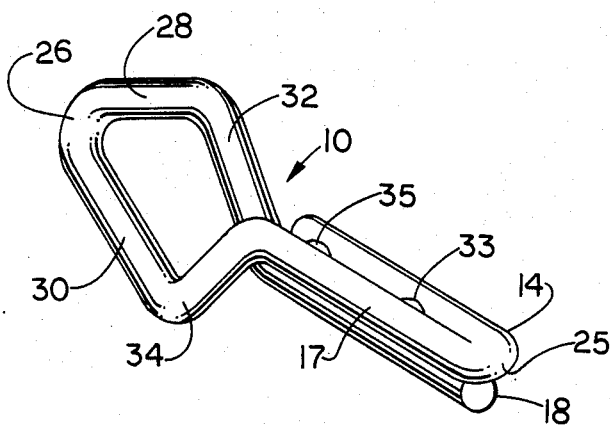
FIG. 10 is a view in perspective of the main section piece of the blank assembly in formed and closed condition before assembly with a jaw addition and guide end section.
Figure 11:
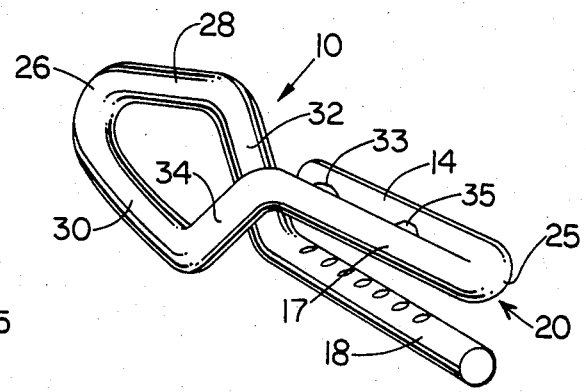
FIG. 11 is a view in perspective of the device of FIG. 10 in open condition.

The main section 12 is formed to a central spring section 26 (FIGS. 10 and 11), diverging first connecting portions 28 and 30 integrally formed with the central spring section 26 and converging second connecting portions 32 and 34, which integrally connect the first connecting portions 28 and 30 to the end portion 18, forming part of the jaw 22, and end portion 17 of jaw 20, respectively. The converging second connecting portions cross as shown in FIGS. 10 and 11. When the main section 12 is in closed position, as shown in FIG. 10, the return bent end portion 14 is parallel to and substantially in face-to-face relation with end portion 17 and overlies the end portion 18. End portions 14 and 17 are rigidly attached to each other by the return bend portion 25 and as by welding at a plurality of locations spaced therefrom, viz., welds 33 and 35.

Figure 7:
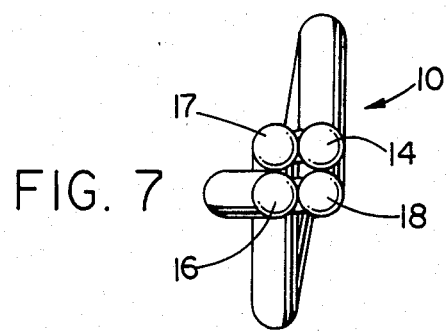
FIG. 7 is a view in end elevation of the aneurysm clip looking in the direction of the arrows 7—7 in FIG. 3.
Figure 8:
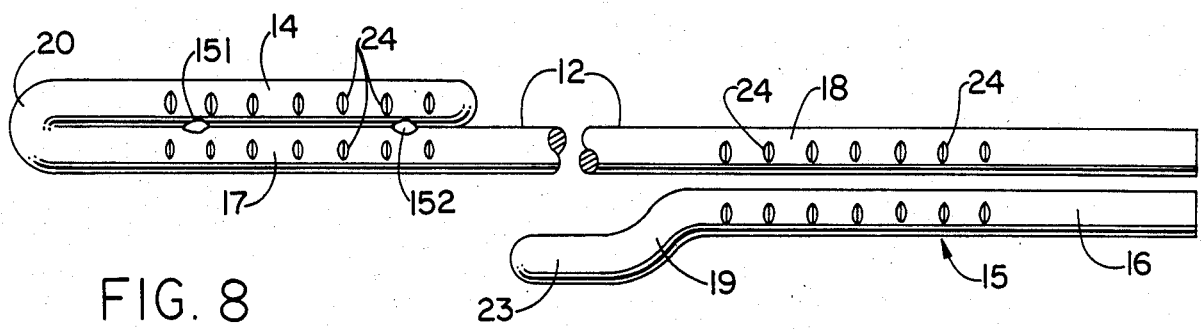
FIG. 8 is a plan view of a two-piece blank assembly from which the aneurysm clip is formed, the pieces being in partly formed condition.
Figure 9:
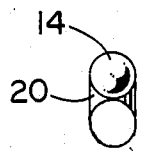
FIG. 9 is a view in end elevation of the partly formed main section blank assembly.

After main section 12 is formed as shown in FIG. 10, it is opened as shown in FIG. 11 and the jaw addition portion 16 of short length 15 is mounted as shown in FIGS. 1-4 and 6-4 on the side of end portion 18 of the main section 12 opposite the side of 18 which correspond to the side of end portion 17 to which return bent end portion 14 is attached. Short length 15 is coplanar with end portion 18 of the main section 12 so that jaws 22 and 20 make opposed contact in a plane when the clip 10 is closed as shown in FIG. 1. The jaw addition portion 16 of short length 15 is substantially in face-to-face parallel relation with the end portion 18 of the main section 12 as shown in FIGS. 1-4, 6 and 7. The short length 15 is longer than the return bend end portion 14 and includes a connecting portion 19 and a guide end portion 23. The jaw addition portion 16 of short length 15 is rigidly attached to the side of the end portion 18 of the main section 12 as shown in FIGS. 8 and 9 as by welding, viz., as by spaced welds 36 and 37, to form jaw 22. The short length 15 is formed to include the guide end portion 23, which is spaced from second connecting portion 32 and end portion 18 of main portion 12. The connecting portion 19 connects the end or guide portion 23 and the jaw addition portion 16 of the short length 15. Slots 24 are formed in faces of the jaws 20 and 22 to improve the non-slip character thereof.

The guide end portion 23 of the short length 15 overlies the second connecting portion 34 so that the converging second connecting portion 34 is held between the end portion 23 and the converging second connecting portion 32 to be guided thereby and so that the jaws 20 and 22 are held in opposed relation. The end portions 17 and 18 of the main section 12 are parallel to each other but are spaced when the clip 10 is in the closed position as shown in FIGS. 1 and 7. The spacing between the end portions 23 of the short length 15 and the converging second connecting portion 32 can be approximately equal to the diameter of the converging second connecting portion 34.

The free end portions of the jaw forming portions 15–18 of jaw 22 are flush with the tip of the free end portion of jaw 20 formed by portion 25 of jaw 20 so that bend portion 25 extends substantially transversely of opposed longitudinal portions 17–18 of jaw 22 to supplement the resistance to longitudinal shifting of the clip resulting from transverse grooves 24.

Where shorter jaws are desired, the jaws may be shortened by cutting off free end portions of the jaws and removing sharp edges resulting from the cut-off operation so the remaining jaws may have a plurality of welds joining portions 14, 17 of jaw 20 and a plurality of welds joining portions 16, 18 of jaw 22, while guide 23 retains the jaws in aligned relation.

The clip 10 can be manipulated and opened by means of an appropriate tool (not shown) such as one of the tools shown in my U.S. Pat. Nos. 2,876,778 and 3,827,438, or my copending application Ser. No. 06/815,388 filed Dec. 31, 1985. The open clip can be positioned to close an aneurysm (not shown) and can be released to seal off the aneurysm.

A preferred method of manufacturing an aneurysm clip embodying the present invention is the method of preparing a main section elongate spring wire blank and a short section elongate spring wire blank, forming the main section blank having a single width jaw at one end to provide a double width jaw adjacent the other end and further forming the blank to clip form with a central curved spring portion at one end of the clip between connecting portions extending to respective jaws at the other clip of the clip urged face-to-face abutment by the spring portion acting through the connecting portions which from the spring portion respectively successively diverge, converge, cross and connect a respective one of the jaws thereby connected to the spring portion, forming the short section blank to have oppositely extending jaw addition and guide portions connected by an intermediate connecting portion supporting the guide portion in parallel relation to the jaw addition portion and offset from alignment therewith, securing the jaw addition portion of the short section to the single width jaw of the main section to form a second double width jaw urged toward face-to-face engagement with the first double width jaw and with the connecting portion of the main section extending from the first double width jaw extending between the guide portion of the short section and the connecting portion of the main section extending from the second double width jaw portion thereof, and removing portions from the ends of the jaws to reduce the jaws to the desired length.

Having described my invention, what I claim as new and desire to secure by Letters Patent is:

1. An aneurysm clip which comprises an elongated main section of spring metal and a pair of short length jaw addition sections attached to end portions of the main section on opposite sides of the main section, the main section being formed to a central spring portion, diverging first connecting portions extending from the central spring portion, converging second connecting portions extending from the first connecting portions, and jaw end portions extending from the converging second connecting portions, the second connecting portions crossing, one of the jaw addition sections including a guide bar extension section extending in overlying relation to one of the second connecting portions associated with an opposed jaw, said one of the second connecting portions being guided between an opposed second connecting portion and the guide bar extension section, the jaw end portions being arranged so that each of the jaw end portions is opposed to one of the short length jaw addition sections, the central spring section urging the jaw end portions toward engaged position with the jaw addition sections.

2. An aneurysm clip as in claim 1 in which the guide bar extension is spaced from said opposed second connecting portion by an amount substantially equal to the diameter of said one of the second connecting portions associated with an opposed jaw.

3. In the manufacture of an aneurysm clip, the method of preparing a main section elongate spring wire blank and a short section elongate spring wire blank, forming the main section blank having a single width jaw at one end and a double width jaw adjacent the other end with a central curved spring portion at the one end of the clip between connecting portions extending to respective jaws at the other end urged to face-to-face abutment by the spring portion, from the spring portion the connecting portions successively diverge, converge, cross and connect the jaws to the spring portion, forming the short section blank to have oppositely extending jaw addition and guide portions connected by an intermediate connecting portion, supporting the guide portion in parallel relation to the jaw addition portion and offset from alignment therewith, securing the jaw addition portion of the short section to the single width jaw of the main section to form a second double width jaw urged toward face-to-face engagement with the first double width jaw and with the connecting portion of the main section extending from the first double width jaw extending between the guide portion of the short section and the connecting portion of the main section extending from the second double width jaw portion thereof, and removing portions from the ends of the jaws to reduce the jaws to the desired length.

* * * * *